United States Patent [19]

Doyle

[11] Patent Number: 4,591,266

[45] Date of Patent: May 27, 1986

[54] PARABOLIC FOCUSING APPARATUS FOR OPTICAL SPECTROSCOPY

[75] Inventor: Walter M. Doyle, Laguna Beach, Calif.

[73] Assignee: Laser Precision Corporation, Utica, N.Y.

[21] Appl. No.: 580,120

[22] Filed: Feb. 14, 1984

Related U.S. Application Data

[63] Continuation of Ser. No. 291,402, Aug. 10, 1981, abandoned.

[51] Int. Cl.[4] .......................... G01J 3/45; G01N 21/01
[52] U.S. Cl. .................................. 356/244; 356/346; 356/440
[58] Field of Search ............... 356/300, 246, 244, 440, 356/133, 319, 320, 321, 322, 323, 324, 325, 436, 437, 438, 439, 73, 346; 250/343, 347, 353

[56] References Cited

U.S. PATENT DOCUMENTS

| | | | |
|---|---|---|---|
| 3,010,358 | 11/1961 | Siegler, Jr. | 356/244 |
| 3,460,893 | 8/1969 | Wilks, Jr. | 356/300 |
| 3,811,749 | 5/1974 | Abel | 350/294 X |
| 3,972,618 | 8/1976 | Hawes | 356/345 |

Primary Examiner—Vincent P. McGraw
Assistant Examiner—Robert D. V. Thompson, III
Attorney, Agent, or Firm—Thomas J. Plante

[57] ABSTRACT

An accessory for use in the sample region of a spectrometer is disclosed which combines a matched pair of off-axis paraboloid reflectors having their focii optically imaged on the sample (either imaged at a common point or at two points which are optically imaged on each other) and having relative locations and orientations such that each ray of radiation strikes the two reflectors at points on the reflectors having approximately the same focal lengths. This arrangement involves the use of collimated optical beams into and out of the accessory. The accessory may function as a transmission-type accessory, in which the radiation passes through the sample, or as an internal reflectance accessory, in which the radiation passes through the sample holder but is reflected by the sample. The focal length relationship set forth is accomplished by having "back-to-back" paraboloid reflectors, i.e., their reflecting surfaces face in substantially different, preferably opposite, directions. A further aspect is the incorporation of means for adjusting the position of at least one of the paraboloid reflectors along a first line parallel to, and along a second line perpendicular to, the axis of the collimated optical beam reflected by the position-adjustable reflector.

5 Claims, 10 Drawing Figures

PARABOLIC FOCUSING APPARATUS FOR OPTICAL SPECTROSCOPY

This is a continuation of application Ser. No. 291,402 filed Aug. 10, 1981, now abandoned.

BACKGROUND OF THE INVENTION

This invention relates to optical spectroscopy, and particularly to focusing accessories for use in directing the radiation to, and receiving the radiation from, a sample under analysis.

Such accessories may conveniently be considered in two general categories. One category (see Doyle Application Ser. No. 298,067, filed Aug. 31, 1981, now U.S. Pat. No. 4,473,295 and having the same assignee as this application) includes reflectance accessories in which the radiation leaving the sample holder is traveling in a different direction from the radiation reaching the sample holder, because of its reflectance by the sample.

The other category, which is of primary interest in the present application, includes accessories in which the radiation leaving the sample holder is traveling in essentially the same direction as the radiation reaching the sample holder. This category, in turn, comprises transmission-type accessories in which the radiation passes through the sample, and multiple internal reflectance (MIR) accessories in which the radiation enters at one end of a sample holder providing an enclosed reflecting path and is reflected several (or numerous) times before leaving the sample holder. The latter type is also commonly identified as attenuated total reflection (ATR).

Where the apparatus of the present invention is used for transmission-type spectroscopy, it will be of particular interest in "micro-sampling," which involves beam condensing for use with small samples, micro pellets and liquid cells. In general, larger samples are adequately handled by the basic focusing system of the spectrometer, but smaller samples require the use of shorter focal lengths in order to concentrate sufficient light at the sample. And shorter focal lengths are more likely to have optical aberration problems.

Where the apparatus of the present invention is used for MIR (or ATR) spectroscopy, it will be of particular interest because of its positional adjustability to accommodate different positions of the sample holder, and also because of its dual function as a beam condensing and an MIR accessory.

Various accessories are available for the functions under discussion. An example of a beam condenser accessory is illustrated on sheet 16 of the loose-leaf, undated catalogue of Harrick Scientific Corporation. Such accessories generally use several mirrors to adequately diverge the beam and refocus it at a smaller spot. They require a number of internal adjustments, and little free space is available for a sample holder.

An example of an internal reflection (MIR) attachment is illustrated on sheet 12 of the same catalogue of Harrick Scientific Corporation. Such a device has additional cost because it is a separate accessory from the beam condenser, and it also has the deficiency of requiring a somewhat complex and sensitive adjustment of mirror positions.

In order to provide an ideal accessory to accomplish the functions discussed above, the following features are considered important:

(1) Locating the sample so that it does not interfere with the optical path;
(2) Minimizing optical aberrations in the accessory;
(3) Using a single accessory for both beam condensing and MIR purposes;
(4) Avoiding a requirement for X, Y, or Z translational adjustments of the whole accessory;
(5) Providing adjustments which permit moving the image point without introducing aberrations;
(6) Using a minimum number of optical elements; and
(7) Reducing the criticality of the requirements for internal adjustments when the accessory is installed.

Although reflectance accessories of the type disclosed herein can be used with a wide variety of spectrometers, they are particularly suited for use with Fourier Transform Infrared (FTIR) instruments, and make use of the fact that the sample region beams in these instruments can be made available in a collimated form with a circular cross section.

SUMMARY OF THE INVENTION

The present invention provides an accessory for optical spectroscopy, which combines a matched pair of off-axis paraboloid reflectors having their focii optically imaged on the sample (either imaged at a common point or at two points which are optically imaged on each other) and having relative locations and orientations such that each ray of radiation strikes the two reflectors at points on the reflectors having approximately the same focal lengths. This arrangement involves the use of collimated optical beams into and out of the accessory. The accessory may function as a transmission-type accessory, in which the radiation passes through the sample, or as an internal reflectance accessory, in which the radiation passes through the sample holder but is reflected by the sample.

The focal length relationship set forth in the preceding paragraph is accomplished by having "back-to-back" paraboloid reflectors, i.e., their reflecting surfaces face in substantially different, preferably opposite, directions.

A further aspect of the present invention is the incorporation of means for adjusting the position of at least one of the paraboloid reflectors along a first line parallel to, and along a second line perpendicular to, the axis of the collimated optical beam reflected by the position-adjustable reflector.

DETAILED DESCRIPTION OF SPECIFIC EMBODIMENTS

Figure 1:
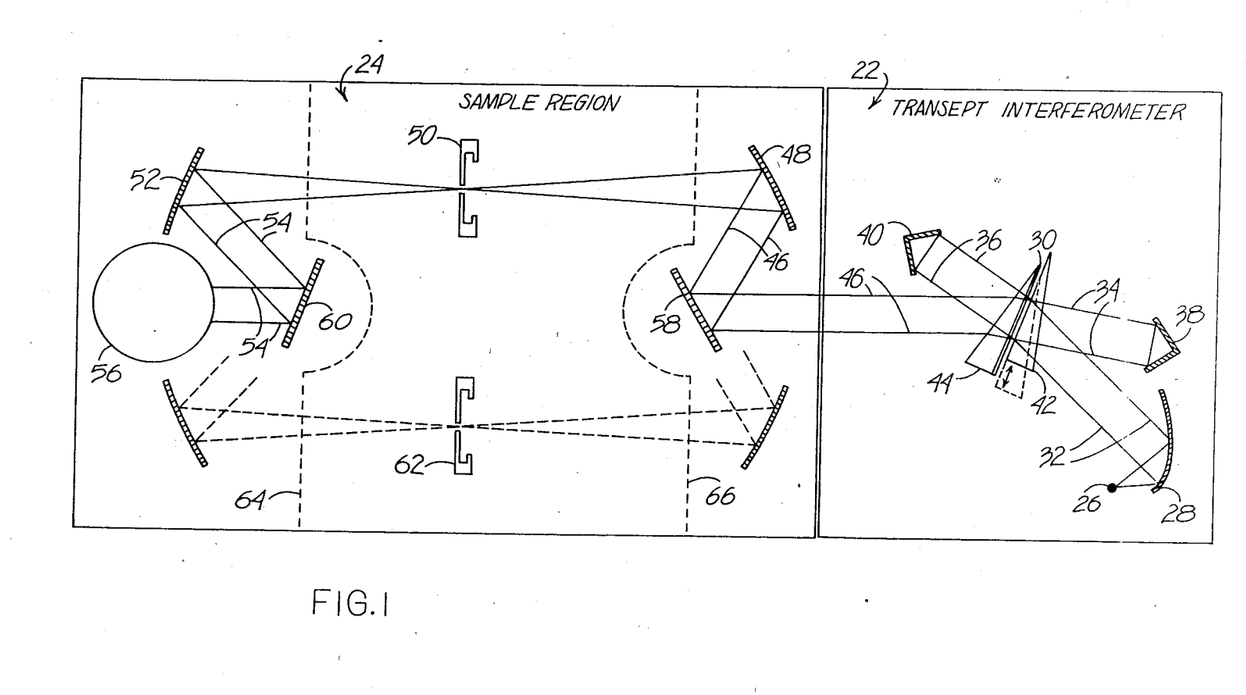
FIG. 1 is a schematic showing the optical components of a spectrometer being marketed by the assignee of the present application, the figure showing the basic unit comprising a "transept interferometer" portion and a "sample region" portion.

FIG. 1 shows an appropriate environment for the use of an optical accessory incorporating the concepts of the present invention. However, the use of the present invention is not limited to the type of spectrometer shown in FIG. 1.

The spectrometer shown is based on several inventions having the same assignee as the present application, including the inventions disclosed in Doyle U.S. Pat. Nos. 4,165,938, issued Aug. 28, 1979; 4,190,366, issued Feb. 26, 1980; and 4,265,540, issued May 5, 1981.

The prior patents referred to were concerned primarily with the interferometer portion of the spectrometer, which is labeled "Transept Interferometer" in FIG. 1 and is generally indicated by numeral 22. The present application is primarily concerned with the sample illuminating portion of the spectrometer, which is labeled "Sample Region" in FIG. 1 and is generally indicated by numeral 24.

The interferometer portion 22 includes a radiation source 26; a paraboloid reflecting mirror 28; a beamsplitter coating 30 which partially reflects and partially transmits the radiation beam 32 coming from mirror 28; two interferometer "arms" provided by the reflected radiation beam 34 and the transmitted radiation beam 36; two stationary retro-reflectors 38 and 40 which constitute the "ends" of the respective interferometer arms; a movable wedge-shaped prism 42 which moves across the path of beam 34 to cause refractive scanning; and a compensating stationary wedge-shaped prism 44 which carries the beamsplitter coating 30.

The operation of the interferometer portion has been fully described in the prior patents referred to above, which are incorporated herein by reference for the purpose of providing a more detailed disclosure of the interferometer portion of the spectrometer.

Attention is called to the fact that the radiation beams 32, 34 and 36 in the interferometer portion are all in collimated form. And the output beam 46 from the interferometer portion is also in collimated form.

In the basic version of the spectrometer shown in FIG. 1, the sample region contains an off-axis paraboloid reflector 48 which receives the collimated beam 46 and focuses it at the sample supported in a sample holder 50, and an off-axis paraboloid reflector 52 which receives the diverging beam after it passes through the sample and provides a collimated output beam 54 transmitted to a detector 56. Two flat mirrors 58 and 60 may be provided at opposite sides of the sample region to direct the incoming beam 46 to paraboloid 48 and to direct the output beam 54 from paraboloid 52 to detector 56.

As shown by the dotted lines illustrating optical rays in the lower part of the sample region, the flat mirrors 58 and 60 may both be rotated to alternate positions to direct a focusing beam to, and receive a diverging beam from, a second sample holder 62. This position-switching of mirrors 58 and 60 provides a dual beam capability for interleaved background measurements. In such usage, the output beam of the interferometer is switched alternately between two similar paths, one serving as a sample path and the other as the background path. In this case, a single scan output display corresponds to the ratio between one sample spectrum and one background spectrum. For a multiple scan measurement, the alternate sample and background spectra are independently averaged, and an updated ratio is computed after each pair of scans. When an accessory, such as the reflecting accessory disclosed in this application, is inserted into the spectrometer, the collimated beam portion of the sample region having the flat mirrors (note description below) can be reserved for accessory interfacing, while the other beam remains in the normal focused configuration.

The present invention is particularly useful as an accessory which can be inserted in the sample region 24 with little or no change in the basic spectrometer as shown in FIG. 1. It is insertable between the input beam 46 received by the sample region from the interferometer portion 22 and the output beam 54 directed to the detector 56. Since the dashed lines 64 and 66 in FIG. 1 outline the sample chamber, the accessory may be designed to fit in the area between those. However, the present invention can be incorporated into spectrometers in many other arrangements.

Figure 2:
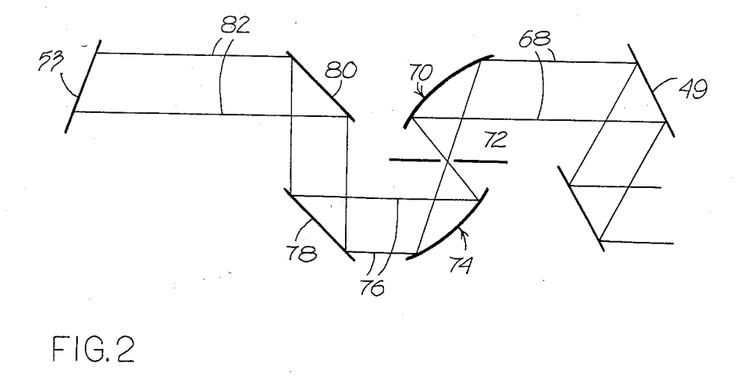
FIG. 2 is a schematic showing a micro-sampling accessory, of the type disclosed in this application, installed in the sample region of the spectrometer of FIG. 1.

The radiation beam entering the accessory, and the radiation beam leaving the accessory, need to be collimated, for reasons which will become apparent during the following description. Accordingly, in order to insert the accessory into the existing sample chamber of FIG. 1, it is necessary to replace the paraboloid reflectors 48 and 52 with flat reflectors. FIG. 2 shows a flat mirror 49 replacing paraboloid 48 and a flat mirror 53 replacing paraboloid 52.

As shown in FIG. 2, a collimated radiation beam 68, which is in effect a continuation of collimated beam 46 from the interferometer, enters the right side of the sample chamber, and is reflected by a first off-axis paraboloid reflector 70 in such a way as to focus at the point where it passes through a sample supported by a sample holder 72. The diverging beam leaving the sample strikes a second off-axis paraboloid reflector 74, which also has its focal point at the sample. The second paraboloid 74 provides a collimated reflected beam 76 which is transmitted to the detector. In the configuration shown, two flat mirrors 78 and 80, which are at angles of 45° to the impinging radiation, are used to realign the exiting beam 82 with the entering beam 68. This realigning of the beam is only necessary because the entering and exiting beams are aligned in the basic layout of the sample region of the spectrometer.

The accessory shown schematically in FIG. 2, which is intended for use as a micro-sampling accessory, is very simple structurally, but it has significant functional advantages over other such accessories because of the orientation of the components. Essentially, it comprises a pair of matched paraboloids 70 and 74, which reflect entering and exiting collimated beams, and which both focus at the sample.

The orientation of the paraboloids 70 and 74 is unique because they are so arranged that the distance between the sample and the point where a given ray of radiation strikes one of the paraboloids is substantially equal to the distance between the sample and the point where the same ray of radiation strikes the other paraboloid. In order to accomplish this, the two paraboloid reflectors 70 and 74 must "face" away from each other, i.e., the entering beam 68 which is reflected by paraboloid 70 and the exiting beam 76 which is reflected by paraboloid 74 must enter and exit the sample chamber at locations generally "opposite" one another. The aberration compensation which is accomplished with the orientation set forth in this paragraph is not obtained when the paraboloids are oriented as are reflectors 48 and 52 in FIG. 1, e.g., facing in directions which are not "opposite," or away from one another.

It is applicant's belief that the entering and exiting collimated beams 68 and 76 should be parallel to one another, i.e., have no angular divergence in direction. In other words, the axes of the two paraboloids 70 and 74 should be anti-parallel, i.e., the apices of the two full parabolas from which the sections are cut should be oppositely directed. However, a mathematical support for this belief has not been developed.

Figure 3:
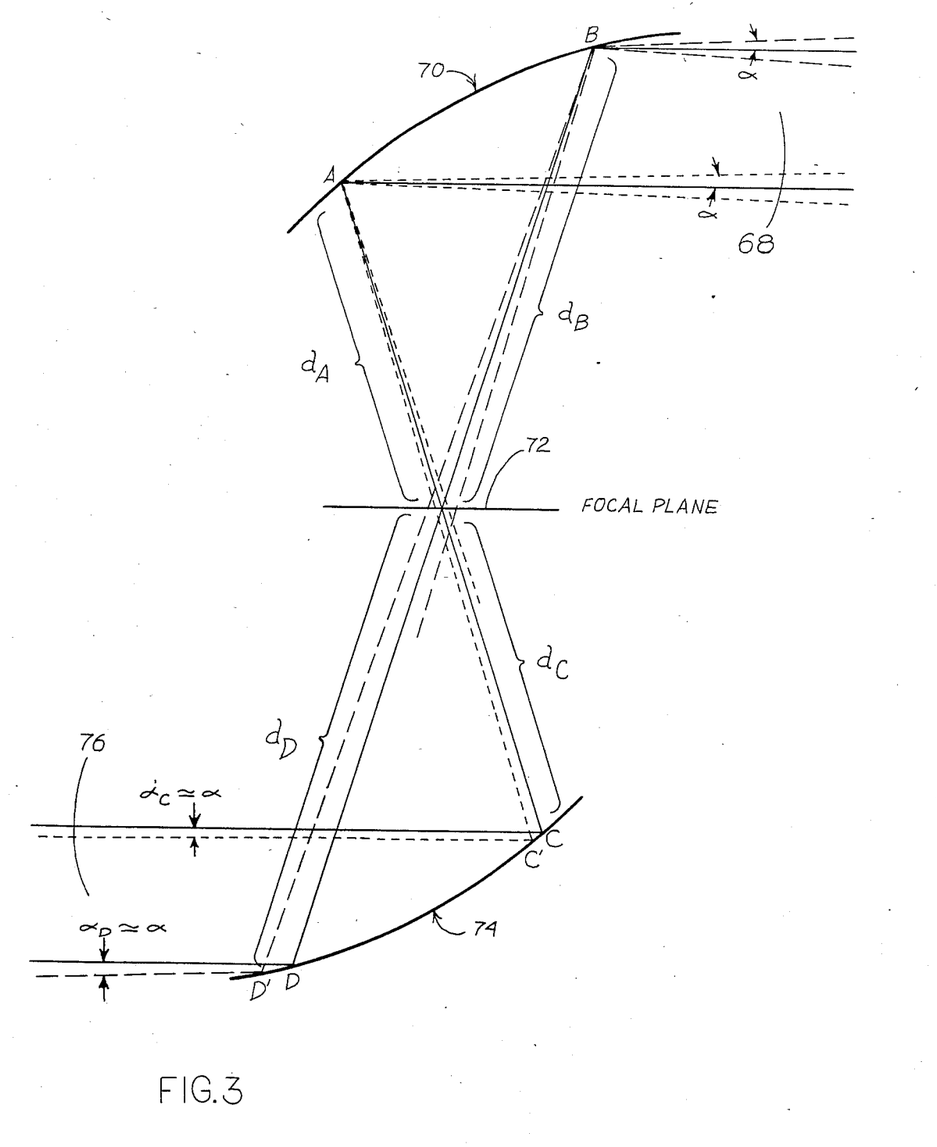
FIG. 3 is a schematic demonstrating that oppositely facing paraboloids, such as those in FIG. 2, provide essentially aberration-free radiation output.
Figure 4:
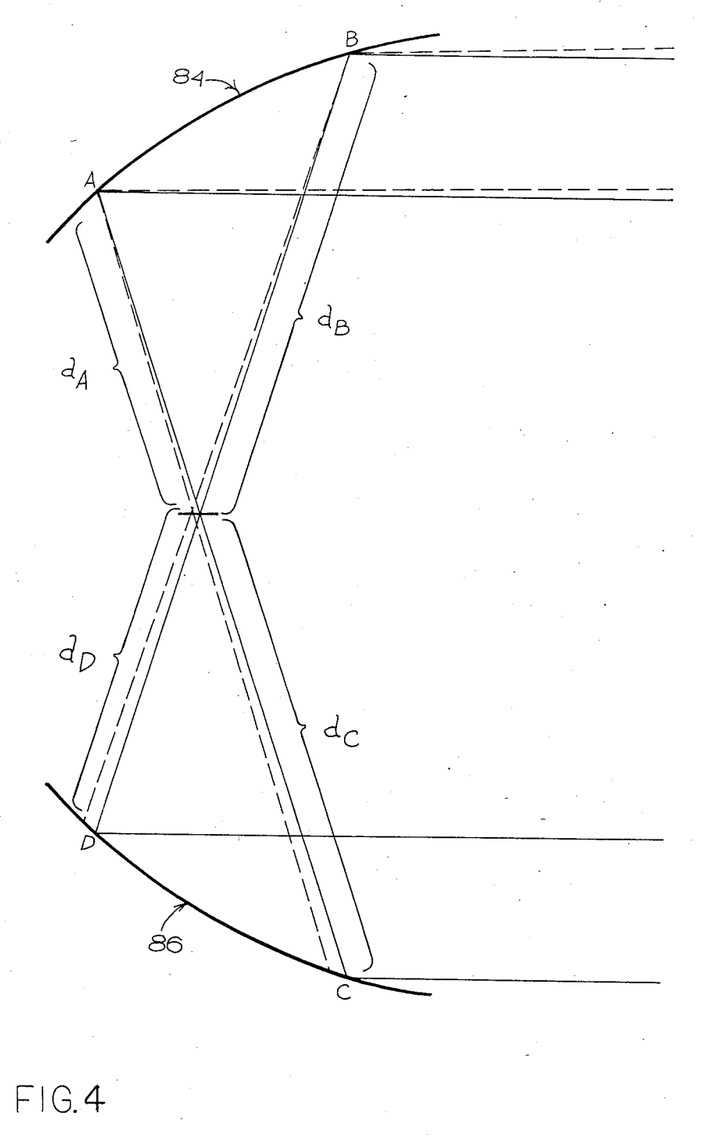
FIG. 4 is a schematic showing paraboloids so oriented that aberration compensation is lacking.

The reasons for the paraboloid orientation shown in FIG. 2 will now be explained in detail, referring to FIGS. 3 and 4. FIG. 3 shows the aberration compensation which results from placing the two paraboloids in positions which generally face away from one another, i.e., in positions such that the entering and exiting radiation beams are moving in the same general direction (from right to left in the drawings). FIG. 4, which is included for comparison purposes, shows a design which does not provide aberration compensation because a given ray, or bundle or rays, will be reflected from locations on the two paraboloids having substantially different focal lengths.

To analyze the compensating effect of the arrangement in FIG. 3, consider an incident light beam having a divergence half angle of $\alpha$. The light striking a given point (such as point B) on the first paraboloid mirror 70 will fall within a bundle of rays having extreme angles of $\pm\alpha$ as shown in FIG. 3. After reflection from the surface of mirror 70, the extreme rays will still make angles of $\pm\alpha$ with the central ray.

We must now consider the characteristics of the image formed in the mirror focal plane, which is the sample location 72. The central rays from each part of the parabolic mirror will all pass through a single point, the focal point. However, the extreme rays will be displaced from the focal point by various distances. For example, an extreme ray from point B will be displaced a distance $x_B \simeq \alpha \cdot d_B$ (or $\alpha \simeq x_B/d_B$), where $\alpha$ is expressed in radians, and $d_B$ represents the distance from point B to the focal plane. And a ray from point A (on mirror 70) will be displaced a lesser distance $x_A \simeq \alpha \cdot d_A$ (or $\alpha \simeq x_A/d_A$), where $d_A$ represents the distance from point A to the focal plane. Another way to look at this is to say that the regions around points A and B represent approximately spherical imaging devices with focal lengths $d_A$ and $d_B$, and thus yield images in the focal plane with radii proportional to these focal lengths.

After passing through the focal plane, the radiation eventually strikes the second parabolic mirror 74 and is approximately recollimated. The divergence of each bundle of rays will depend on the focal length of the region of the paraboloid 74 which it strikes. For example, the rays coming from the part of the image with radius $x_B$ will strike the region around point D. Their divergence will thus be $\alpha_D \simeq x_B/d_D$ ($d_D$ representing the distance from point D to the focal plane). But we have $d_D$ approximately equal to $d_B$ ($d_D \simeq d_B$). Therefore, $\alpha_D \simeq x_B/d_B \simeq \alpha$. Also $\alpha_C \simeq x_A/d_C$ ($d_C$ representing the distance from point C to the focal plane). Since $d_C$ is approximately equal to $d_A$ ($d_C \simeq d_A$), it follows that $\alpha_C \simeq x_A/d_A \simeq \alpha$. So the divergence angle, represented by $\alpha$, has been approximately preserved from the entering collimated beam 68 to the exiting collimated beam 76.

FIG. 4 is an example of a design lacking aberration compensation. In this figure both paraboloid mirrors 84 and 86 face toward the right, with the result that $d_D$ is not approximately equal to $d_B$, and $d_C$ is not approximately equal to $d_A$. As previously stated, it appears that maximum aberration cancellation will occur only if the two paraboloids are positioned with their axes anti-parallel, i.e., with the paraboloids "facing" in opposite directions, as in FIGS. 2 and 3.

Figure 5:
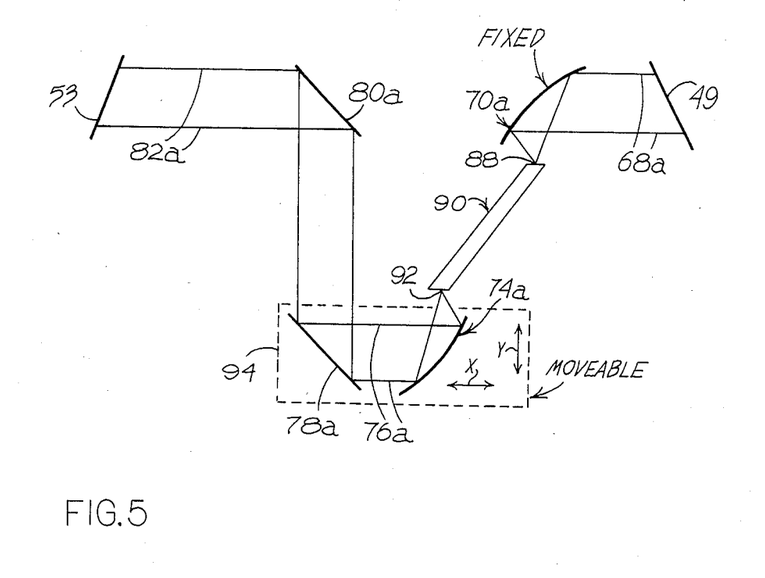
FIG. 5 is a schematic showing an accessory similar to that of FIG. 2, but incorporating an adjustably positioned paraboloid to accommodate sample holders having spaced image points, such as a multiple internal reflectance device or a light pipe.

FIG. 5 shows an adjustable design which allows the two paraboloids to be focused at the ends of a device such as a light pipe, or a multiple internal reflection (MIR) plate. Only two adjustments are provided, which are orthogonal. This greatly simplifies the alignment procedure required to compensate for light piping elements, or internal reflection elements, having various lengths or angular positions.

The arrangement shown schematically in FIG. 5, and shown in greater detail in the remaining figures, is the preferred embodiment because of its universality. It can be used as a micro-sampling accessory, or with an MIR plate or light pipe, because of its adjustability.

When used with an MIR plate or light pipe, as shown in FIG. 5, the convenient, and essentially error-free, adjustability of the accessory is more significant than its aberration-compensating advantage.

As shown in FIG. 5, the collimated entering beam 68a is reflected by a fixed paraboloid reflector 70a to focus at point 88, which is at one end of a sample-containing element, or sample holder, 90. A second, movable paraboloid reflector 74a has its focal point at 92, which is the other end of sample holder 90. Paraboloid 74a reflects a collimated exiting beam 76a, which may be realigned with entering beam 68a by means of two flat mirrors 78a and 80a to provide a collimated beam 82a for the detector. The focal point 92 of paraboloid 74a may be regarded as a "transferred", or "secondary", focal point of the paraboloid 70a; and the focal point 88 of paraboloid 70a may be regarded as a "transferred", or "secondary", focal point of the paraboloid 74a. As stated in the "Summary of the Invention", focal points 88 and 92 are optically imaged on each other.

The position of movable paraboloid 74 may be adjusted along a line parallel to the collimated beams 68a and 76a, as shown by arrows X, or along a line perpendicular to the collimated beams 68a and 76a, as shown by arrows Y. These orthogonal adjustments permit the accessory to accommodate various lengths and angular positions of the sample holder 90. Also, adjustment may be desirable in some micro-sampling uses where the sample through which the radiation passes is unusually thick.

It is important that the position adjustment of movable paraboloid 74a be appropriately constrained, in order to retain maximum reliability of the instrument. Since the beam leaving the movable paraboloid 74a is collimated, the accuracy of the instrument is ensured if the mechanical adjustment motion of the paraboloid is only along the direction of the collimated beam. The imaging characteristics are therefore unchanged by the adjustment, and good focus is maintained.

In order to ensure that repositioning of the movable paraboloid does not introduce aberrations, the axis of rotation of the movable paraboloid (the symmetrical axis of the complete parabola) must remain parallel to the collimated radiation beam emerging from it. One way of ensuring this is to confine motion of the movable paraboloid to pure translation, i.e., movement which does not involve any rotation. And the preferred way of limiting the motion to pure translation is to provide for orthogonal motion only, i.e., motion either parallel or perpendicular to the collimated beam.

There are different combinations of adjustable components which will have the desired result. If only paraboloid 74a is moved in direction X, while mirrors 78a and 80a remain stationary, the collimated beam will remain aligned. And if paraboloid 74a and mirror 78a are moved in direction Y, as by moving a platform 94 shown in dashed lines, while mirror 80a remains stationary, the collimated beam will remain aligned.

The detailed construction shown in the remaining figures is designed to move as a unit all three elements (paraboloid 74a, and mirrors 78a and 80a) when adjustment is made in direction X, and to move as a unit two elements (paraboloid 74a and mirror 78a) when adjustment is made in direction Y.

Figure 6:
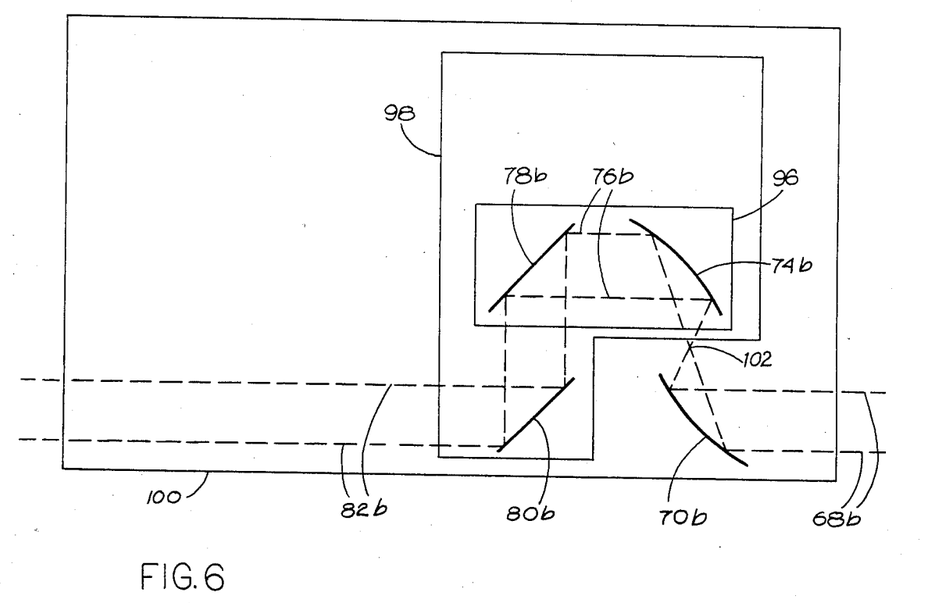
FIGS. 6 and 7 are schematics showing two working positions of an accessory having a paraboloid whose position is adjustable, FIG. 6 showing it in position to accommodate a transmission-type sample holder, and FIG. 7 showing it in position to accommodate a sample holder having spaced image points.
Figure 7:
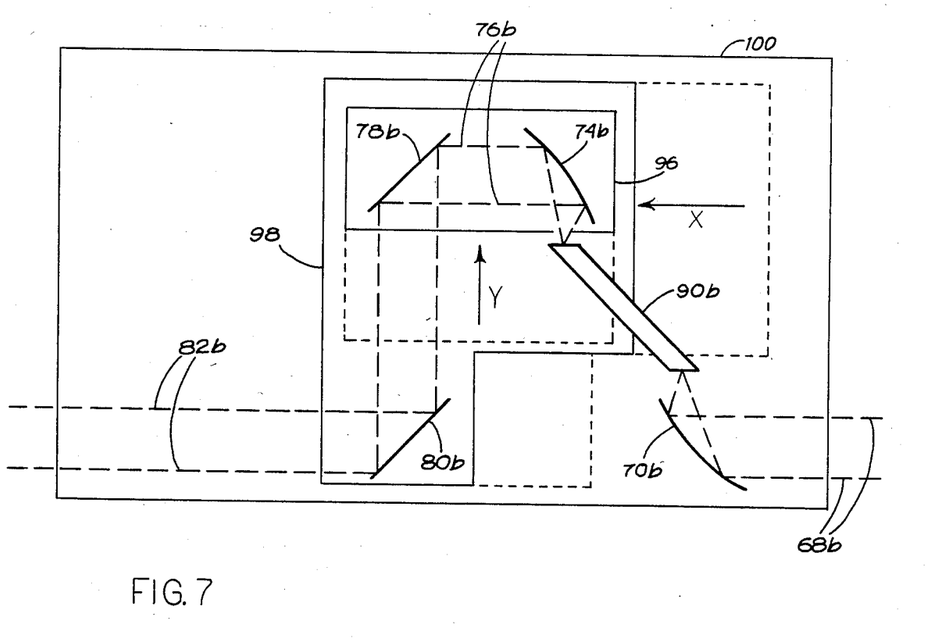

FIGS. 6 and 7 show schematically two possible working positions of a paraboloid whose position is adjustable to accommodate different types of sample holders. As seen in those figures, a movable paraboloid reflector 74b is carried by a first movable supporting member, or plate, 96 which is in turn carried by a second, larger movable supporting member, or plate, 98. As shown by the arrows in FIG. 7, the first plate 96 is constrained to move linearly along the second plate 98, and the second plate 98 is constrained to move linearly along an accessory-supporting platform 100. One of the flat mirrors 78b, which initially reflects the collimated beam 76b coming from movable paraboloid 74b, is mounted on the first supporting plate 96; and the other flat mirror 80b, which reflects the beam coming from mirror 78b to direct the collimated beam 82b toward the detector, is mounted on the second supporting plate 98, but not on the first supporting plate 96. A first guiding means between the first supporting plate 96 and the second supporting plate 98 causes the first supporting plate to move solely in a direction perpendicular to collimated beam 76b; and a second guiding means between the second supporting plate 98 and the platform 100 causes the second supporting plate to move solely in a direction parallel to collimated beam 76b.

FIG. 6 shows the movable paraboloid 74b in position to accommodate a transmission-type sample holder, because the focal points of the two paraboloids coincide at point 102. The paraboloid 70b, which receives the entering collimated beam 68b, will generally be mounted in a fixed position, although it is conceivable that either or both paraboloids could be adjustably positioned.

FIG. 7 shows that movable paraboloid 74b in position to accommodate an internal reflectance-type sample holder 90b, which requires that the focal points of the two paraboloids be at spaced locations, as shown. The first supporting plate 96, carrying movable paraboloid 74b and flat mirror 78b, has been moved upwardly, as viewed in the figure; and the second supporting plate 98, carrying the first supporting plate and flat mirror 80b, has been moved leftwardly, as viewed in the figure. The positions which the movable members had in FIG. 6 are shown in dashed lines in FIG. 7.

Figure 8:
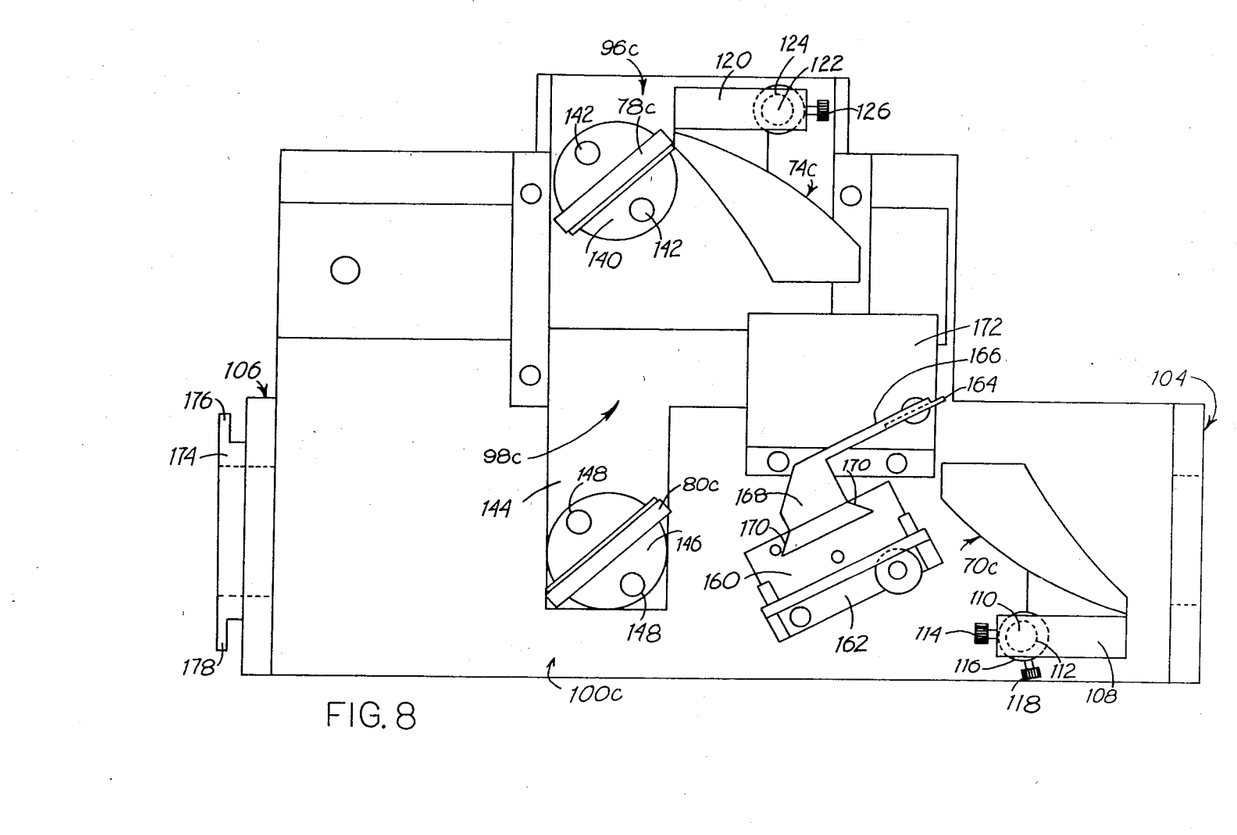
FIG. 8 is a plan view of a complete accessory constructed in accordance with the principles of the present invention, on which is mounted a sample holder designed for light transmission through the sample.
Figure 9:
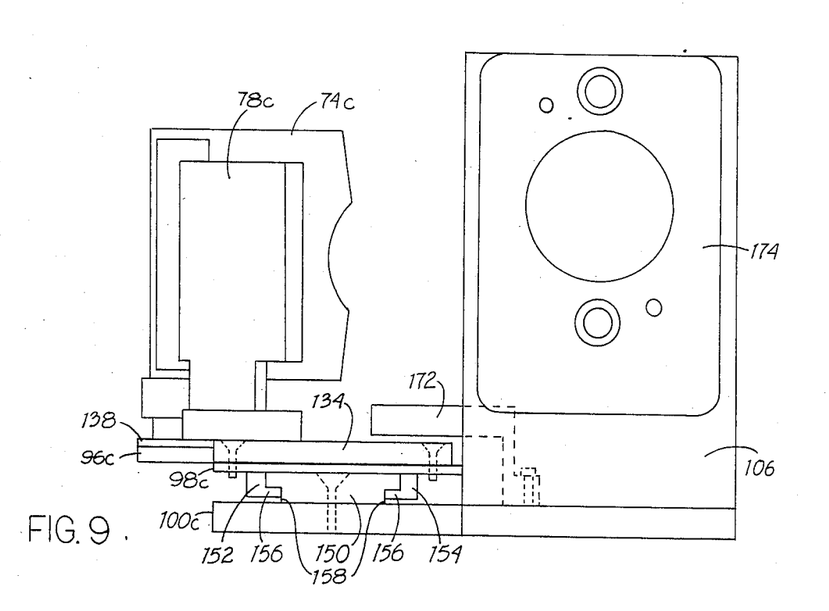
FIGS. 9 and 10 are elevation views of the accessory shown in FIG. 8, FIG. 9 showing an end view and FIG. 10 a side view.
Figure 10:
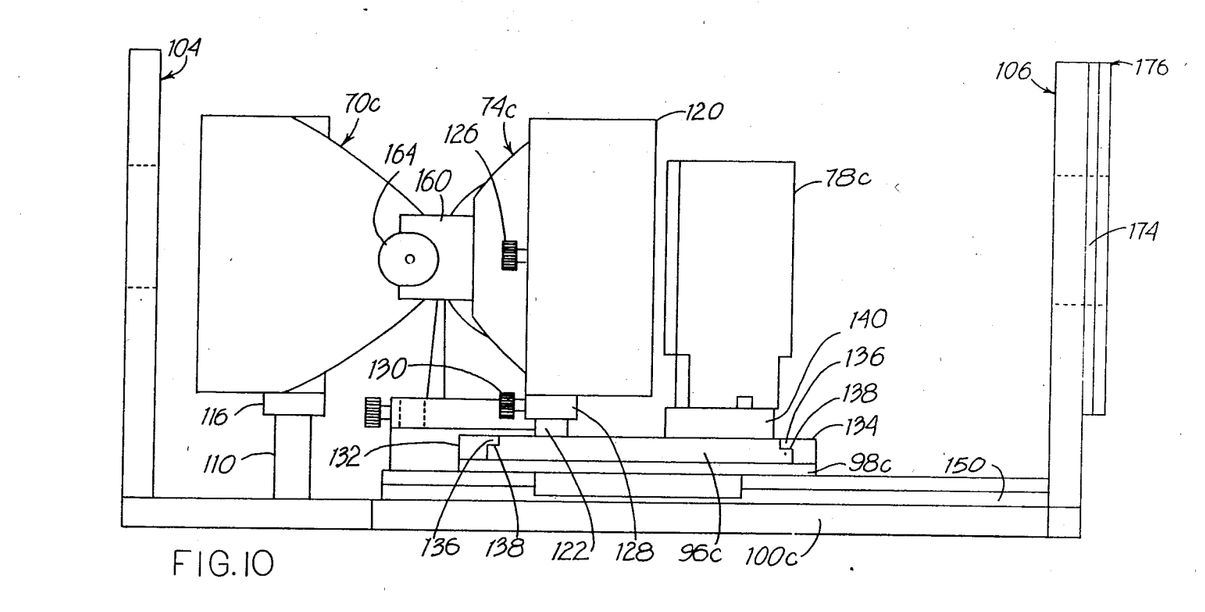

FIGS. 8–10 provide a more detailed showing of a specific accessory design having the desired characteristics. The accessory is a unitary structure having an overall supporting platform, or base plate, 100c, which carries two end plates 104 and 106, the former having an aperture for the entering radiation beam, and the latter having an aperture for the exiting radiation beam.

The fixed paraboloid 70c, which is located close to end plate 104 and which receives the entering radiation beam, is shown secured to an adjustable mount 108. The mount 108 is supported on a vertical post 110 (see FIG. 10), which is secured to the base plate 100c. In order to permit initial focal adjustment of the fixed paraboloid, the mount 108 has a vertical bore 112 therein (see FIG. 8) into which the post 110 extends, thus permitting rotational movement of the mount. A set screw 114 may be used to lock the mount in its adjusted position. Vertical support and adjustment of the position of mount 108 may be provided by a vertical stop, in the form of a collar 116 which encircles the post and which is locked into position after vertical adjustment by a set screw 118.

The movable paraboloid 74c is supported on the first movable supporting plate 96c, which in turn is supported on the larger second movable supporting plate 98c; and the entire structure is, of course, mounted on the platform 100c. In order to more clearly show the shape of the second supporting plate 98c, including its integral arm 144 which carries mirror 80c, the first plate 96c is shown out of position in FIG. 8, i.e., it has been moved upward (along the Y axis) from its normal position, in which paraboloid 74c is the same distance from the sample holder as paraboloid 70c.

The movable paraboloid 74c is shown as having the same initially adjustable mounting as the fixed paraboloid 70c. Paraboloid 74c is secured to an adjustable mount 120, which is supported on a vertical post 122 secured to supporting plate 96c. In order to permit initial focal adjustment of the movable paraboloid, the mount 120 has a vertical bore 124 therein into which the post 122 extends, thus permitting rotational movement of the mount. A set screw 126 may be used to lock the mount in its adjusted position. Vertical support and adjustment of the position of mount 120 may be provided by a vertical stop, in the form of a collar 128 which encircles the post and which is locked into position after vertical adjustment by a set screw 130.

As best seen in FIG. 10, the motion of paraboloid 74c to adjust its position along the Y axis is permitted but confined by sliding of the first supporting plate 96c between two guides 132 and 134 secured to the second supporting plate 98c. Each of the guides 132 and 134 has a flange 136 engaging a corresponding ledge 138 formed on plate 96c, thereby clamping plate 96c to plate 98c.

The flat mirror 78c is also supported on the first supporting plate 96c, and is initially adjustable by movement of its platform 140, which is secured to plate 96c by fasteners 142 extending through slightly oversize holes.

The flat mirror 80c is supported on a projecting arm 144 of the second supporting plate 98c. Mirror 80c is initially adjustable by movement of its platform 146, which is secured to plate 98c by fasteners 148 extending through slightly oversize holes. Mirror 80c may also have adjustability on a hinged horizontal shaft (not shown).

As best seen in FIG. 9, the motion of paraboloid 74c to adjust its position along the X axis is permitted but confined by sliding of the second supporting plate 98c along the top of a rail 150 which is secured to base plate 100c. The supporting plate 98c is shown supported on rail 150, and is confined to linear motion by guides 152 and 154 secured to the bottom of plate 98c on opposite sides of rail 150. Each of the guides 152 and 154 has a tongue 156 extending into a corresponding groove 158 formed in rail 150, thereby clamping plate 98c to the base plate, or platform, 100c.

The sample holder shown in FIGS. 8–10 is the type used for transmission spectroscopy, i.e., spectroscopy having a single focal point of the two paraboloids. It is so located and designed that the transmission-type sample holder may easily be removed and replaced with a sample holder used in spectroscopy requiring spaced focal points of the two paraboloids. The sample holder shown has a mount 160 which is secured to a vertical support 162 mounted on platform 100c. The vertical support 162 may be initially adjusted by means of fasteners extending through slightly oversize holes in the base plate. The sample may be carried in a micro-sample disc 164, which fits into a slot in an arm 166 of a sample holder 168. The sample holder 168 is supported on mount 160 in such a way as to have initial adjustment both along a vertical line and along a horizontal line. The vertical adjustment may be guided by a dovetail connection 170 between the sample holder 168 and the mount 160; and the horizontal adjustment may be guided by a similar dovetail connection (not visible) between the mount 160 and its vertical support 162.

The figures also show a sample holder platform 172 secured to platform 100c, which is the support used for sample holders when spectroscopy other than transmission-type spectroscopy is being performed.

The end plate 106 through which the exiting radiation beam passes is shown with a guide plate 174 secured thereon, which is used in precisely locating the accessory in the sample chamber of the complete spectroscopic instrument. The original sample holder 50 (see FIG. 1) may be repositioned and located by mounting holes provided in the complete instrument. Then lowering the accessory into position with vertical tongues 176 and 178 (on opposite sides of guide plate 174) engaging complementary slots in sample holder 50 will automatically provide the correct location for the accessory in the complete instrument.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. For use with a spectrometer having a collimated radiation beam approaching a sample and a collimated radiation beam leaving the sample, an optical accessory, of the type in which radiation is passed through a sample holder element which provides a confined path therethrough, comprising:

a first paraboloid reflector which reflects the approaching collimated beam in such a way as to focus the radiation at one end of the confined radiation path through the sample holder;

a second paraboloid reflector which receives radiation from a focus at the other end of the radiation path through the sample holder and which reflects the radiation to provide the collimated beam leaving the sample; and means for allowing constrained adjustment movement of at least one of the paraboloid reflectors relative to the other paraboloid reflector in order to adjust for differences in the length and/or orientation of the sample holder element, such means including (a) means for allowing such movement of at least one of the paraboloid reflectors along a path parallel to the axis of its incident collimated beam, and (b) means for allowing such movement of at least one of the paraboloid reflectors along a path perpendicular to the axis of its incident collimated beam.

2. The optical device of claim 1 in which the collimated radiation beams approaching and leaving the sample are co-linear, and in which only one of the two paraboloid reflectors is allowed constrained adjustment movement, the optical accessory also comprising:

a first flat reflecting mirror which laterally reflects the collimated beam reflected by the movable paraboloid;

a second flat reflecting mirror which reflects the collimated beam from the first reflecting mirror to cause the approaching and leaving beams to be co-linear;

a first supporting member which carries the first reflecting mirror;

a second supporting member which carries the second reflecting mirror; and linear guiding means between the first and second supporting members which permits relative movement of the two flat mirrors constrained to linear movement along the axis of the collimated beam which travels between them.

3. The optical device of claim 2 wherein:

the first flat reflecting mirror and the movable paraboloid reflector are both mounted on the first supporting member in positions which remain fixed relative to one another;

the first supporting member and the second flat reflecting mirror are both carried by the second supporting member;

the first supporting member is linearly movable on the second supporting member along the axis of the collimated beam between the first and second flat reflecting mirrors; and the second supporting member is linearly movable along the axis of the collimated co-linear approaching and leaving beams.

4. The optical accessory of claim 2 wherein:

the second flat reflecting mirror remains in a fixed position on the second supporting member;

the first flat reflecting mirror and the movable paraboloid reflector are both mounted on the first supporting member; and the movable paraboloid reflector is linearly movable for adjustment purposes on the first supporting member along the axis of the collimated beam between the movable paraboloid reflector and the first flat reflecting mirror.

5. The optical accessory of claim 1 in which the means for allowing constrained adjustment movement comprises:
a first linearly extending guide parallel to the axis of the collimated beam reflected by the movable paraboloid reflector, along which guide the position of the movable paraboloid reflector may be adjusted; and
a second linearly extending guide perpendicular to the axis of the collimated beam reflected by the movable paraboloid reflector, along which guide the position of the movable paraboloid reflector may be adjusted.

* * * * *